United States Patent
Caulier et al.

(10) Patent No.: US 9,903,828 B2
(45) Date of Patent: Feb. 27, 2018

(54) PHOTOTHERMAL EXAMINATION METHOD AND CORRESPONDING EXAMINATION UNIT

(71) Applicant: AREVA NP, Courbevoie (FR)

(72) Inventors: Yannick Caulier, Chalon sur Saone (FR); Matthieu Taglione, Dijon (FR)

(73) Assignee: AREVA NP, Courbevoie (FR)

( * ) Notice: Subject to any disclaimer, the term of this patent is extended or adjusted under 35 U.S.C. 154(b) by 0 days.

(21) Appl. No.: 15/306,949

(22) PCT Filed: Apr. 29, 2015

(86) PCT No.: PCT/EP2015/059421
§ 371 (c)(1),
(2) Date: Oct. 26, 2016

(87) PCT Pub. No.: WO2015/166007
PCT Pub. Date: Nov. 5, 2015

(65) Prior Publication Data
US 2017/0067839 A1    Mar. 9, 2017

(30) Foreign Application Priority Data
Apr. 30, 2014   (FR) .................................... 14 53989

(51) Int. Cl.
| | | |
|---|---|---|
| G06K 9/00 | (2006.01) | |
| G01N 25/72 | (2006.01) | |
| G01J 5/10 | (2006.01) | |
| G06T 7/00 | (2017.01) | |
| G01J 5/00 | (2006.01) | |

(52) U.S. Cl.
CPC ................ *G01N 25/72* (2013.01); *G01J 5/10* (2013.01); *G06T 7/0004* (2013.01); *G01J 2005/0077* (2013.01); *G06T 2207/10004* (2013.01)

(58) Field of Classification Search
CPC .................. G01N 25/72; G06T 7/0004; G06T 2207/10004; G01J 5/10; G01J 2005/0077
See application file for complete search history.

(56) References Cited

U.S. PATENT DOCUMENTS

| 4,578,584 A | * | 3/1986 | Baumann | ............... G01N 23/22 250/338.1 |
|---|---|---|---|---|
| 4,589,783 A | * | 5/1986 | Thomas | ................. G01N 25/72 250/334 |
| 5,118,945 A | * | 6/1992 | Winschuh | ............ G01N 21/171 250/341.4 |

(Continued)

FOREIGN PATENT DOCUMENTS

WO    WO 98/39640    9/1998

OTHER PUBLICATIONS

Search Report of corresponding PCT International Application.
(Continued)

*Primary Examiner* — Amir Alavi
(74) *Attorney, Agent, or Firm* — Davidson, Davidson & Kappel, LLC

(57) ABSTRACT

A photothermal examination method and corresponding examination unit are provided. In the method first and second zones of the surface to be characterized are scanned simultaneously, and first and second photosensitive surfaces separate from one another acquire images of the infrared radiation emitted by these two zones.

27 Claims, 6 Drawing Sheets

(56) References Cited

U.S. PATENT DOCUMENTS

| | | | |
|---|---|---|---|
| 5,365,065 A * | 11/1994 | Power | G01B 11/0666 |
| | | | 250/330 |
| 6,419,387 B1 | 7/2002 | Legrandjacques et al. | |
| 2003/0030002 A1 | 2/2003 | Safai | |
| 2004/0188602 A1* | 9/2004 | Chinn | G01N 21/171 |
| | | | 250/234 |
| 2006/0222047 A1* | 10/2006 | Reading | G01N 25/4833 |
| | | | 374/120 |
| 2010/0292938 A1 | 11/2010 | Vrana et al. | |
| 2012/0288049 A1* | 11/2012 | Renshaw | G01N 25/72 |
| | | | 376/247 |
| 2015/0096381 A1* | 4/2015 | Taglione | G01N 29/262 |
| | | | 73/627 |
| 2017/0067839 A1* | 3/2017 | Caulier | G01N 25/72 |
| 2017/0076458 A1* | 3/2017 | Caulier | G01B 11/2531 |

OTHER PUBLICATIONS

Li et al., "Crack imaging by scanning laser-line thermography and laser-spot thermography;Crack imaging by scanning LTT and LST," XP020191583, Measurement Science and Technology, Feb. 1, 2011, IOP, Bristol, GB—ISSN 0957-0233.

* cited by examiner

PHOTOTHERMAL EXAMINATION METHOD AND CORRESPONDING EXAMINATION UNIT

The invention relates to looking for defects in industrial components in general.

More specifically, according to a first aspect, the invention relates to a photothermal examination method of a part, comprising a first sequence having the following steps:
step 11: scanning a first zone of a surface of the part with a first heat input element, the scanning being done along a plurality of lines substantially parallel to a first direction;
step 12: acquiring an image of the infrared radiation emitted by said first zone using a first photosensitive surface element.

BACKGROUND

Such a method is for example known from WO 98/39640.

According to this method, the first heat input element is a line created by a laser, moved on the surface of the part. A detection zone is also moved on the surface of the part, following the trajectory of the heat input element, with a positive or negative time delay. The detection zone is continuously examined by the first photosensitive surface.

To inspect the first zone, it is necessary to perform four successive scans: an outgoing journey in the first direction, a return in the first direction, an outgoing journey in a second direction, which may be perpendicular to the first, and a return in the second direction.

The examination method is therefore relatively long: the examination time is about 3 to 4 hours per $m^2$ of surface area to be inspected.

SUMMARY OF THE INVENTION

In this context, one aim of the invention is to provide a faster method.

To that end, the invention provides a photothermal examination method of the aforementioned type, characterized in that the method further comprises the following steps:
step 13: scanning a second zone of the surface of the part with a second heat input element, the scanning being done along a plurality of lines substantially parallel to a second direction;
step 14: acquiring an image of the infrared radiation emitted by said second zone using a second photosensitive surface element;
the first and second zones being scanned simultaneously and the first and second photosensitive surfaces being separate from one another;
the second direction forms a first non-zero angle with the first direction, said first angle preferably being larger than 30°, or
the second direction is substantially parallel to the first direction, the first and second heat input elements being lines forming a second non-zero angle between them, said second angle preferably being larger than 30°.

Thus, in the method according to the invention, at least two zones of the surface of the part are scanned simultaneously, with two different heat input elements.

Furthermore, the acquisition of the infrared radiation images is also accelerated, due to the use of two separate photosensitive surface elements, which are therefore capable of performing a simultaneous acquisition.

The fact that the scanning with the first and second heat input elements is done in two directions inclined relative to one another is particularly convenient. Indeed, it is possible, during the first sequence, to scan the first and second zones simultaneously, using the first heat input element and the second heat input element, respectively, then to move the means making it possible to create the heat input elements, such that the second zone is scanned by the first heat input element, the second heat input element scanning a third zone. The second zone is thus scanned during the first sequence in the second direction, then during a second sequence in the first direction.

The rearrangement of the means making it possible to generate the two heat input elements is easy and fast when one goes from the first to the second sequence. Indeed, the journey made by the first and second heat input elements is generally always the same irrespective of the sequence, and is always done in the first direction and the second direction, respectively.

This is also true when the first and second heat input elements are lines forming a second non-zero angle between them, and moving substantially along the same direction. The first sequence makes it possible to scan the second zone with the second heat input element, having a given incline, and the second sequence makes it possible to scan the second zone with the first heat input element, which has another incline.

The method may also have one or more of the features below, considered individually or according to any technically possible combinations.
the first and second photosensitive surface elements are two parts of a photosensitive surface of a matricial sensor;
the method further comprises at least one second sequence having the following steps:
step 21: scanning the second zone of the surface of the part with the first heat input element, the scanning being done along a plurality of lines substantially parallel to the first direction;
step 22: acquiring an image of the infrared radiation emitted by said second zone using the first photosensitive surface element;
step 23: scanning a third zone of the surface of the part with the second heat input element, the scanning being done along a plurality of lines substantially parallel to the second direction;
step 24: acquiring an image of the infrared radiation emitted by said third zone using the second photosensitive surface element;
the second and third zones being scanned simultaneously;
the method comprises a step for moving the first and second photosensitive surface elements relative to the part between the first sequence and the second sequence;
the method comprises, after the first and second sequences:
a first processing step, in which first and/or second final images of the second zone are calculated respectively from images of the infrared radiation emitted by said second zone and respectively collected by the first and/or second photosensitive surface elements, respectively during the second and/or first sequences;
a second processing step, in which any structural defects in the second zone are detected by using the first and/or second final images obtained in the first processing step;

the method is defined as below:

a) during the second sequence, the first heat input element scans the second zone while occupying, at a plurality of successive moments, a plurality of successive positions, and the first photosensitive surface element acquires a plurality of images of the infrared radiation emitted by the second zone at said plurality of moments; and/or b) during the first sequence, the second heat input element scans the second zone while occupying, at a plurality of successive moments, a plurality of successive positions, and the second photosensitive surface element acquires a plurality of images of the infrared radiation emitted by the second zone at said plurality of moments;

and the first processing step comprises the following operations:

c) for each image acquired during the second sequence, determining the given moment from the plurality of moments at which that image was acquired and extracting, from said image, a plurality of first points corresponding to the position of the first heat input element at a second given moment, the second given moment being equal to the given moment plus a predetermined time shift; constituting the first final image by superimposing the first point extracted from all of the images acquired during the second sequence; and/or d) for each image acquired during the first sequence, determining the given moment from the plurality of moments at which that image was acquired and extracting, from said image, a plurality of second points corresponding to the position of the second heat input element at a second given moment, the second given moment being equal to the given moment plus a predetermined time shift; constituting the second final image by superimposing the second point extracted from all of the images acquired during the first sequence;

during the first sequence, the first photosensitive surface element acquires images of the infrared radiation emitted by a first object field containing the first zone, and the second photosensitive surface element acquires images of the infrared radiation emitted by a second object field containing the second zone, the first and second object fields being fixed during the first sequence;

during the first sequence, the first photosensitive surface element acquires images of the infrared radiation emitted by at least all of the first zone, and the second photosensitive surface element acquires images of the infrared radiation emitted by at least all of the second zone;

each zone of the surface of the part is scanned during a sequence with the first heat input element along a plurality of lines parallel to the first direction, and during another sequence with the second heat input element along a plurality of lines parallel to the second direction, images of the infrared radiation emitted by said zone being acquired by the first photosensitive surface element during said sequence and by the second photosensitive surface element during said other sequence; and the first and second heat input elements are generated by a laser with a defined geometric shape, or a continuous or pulsed emission bulb, or an inductive winding;

the second direction is substantially parallel to the first direction, the first heat input element being a line forming, with the first direction, an angle comprised between 20° and 70°, the second heat input element being a line forming, with the second direction, an angle comprised between 110° and 160°;

the method is defined as below:

a) during the second sequence, the first heat input element scans the second zone while occupying, at a plurality of successive moments, a plurality of successive positions, and the first photosensitive surface element acquires a plurality of first images of the infrared radiation emitted by the second zone at said plurality of moments;

and the first processing step comprises the following operations:

c1) for each first image acquired during the second sequence, determining the given moment from the plurality of moments at which said first image was acquired and extracting, from said first image, a line of first points corresponding to the position of the first heat input element at a second given moment, the line comprising a first upstream end point situated furthest along the first direction and a first downstream end point shifted relative to the first upstream end point opposite the first direction and along a first transverse direction perpendicular to the first direction, each first point having a measured intensity representative of the temperature of the surface of the part in a zone corresponding to said first point;

c2) establishing a first differential line by assigning each first point a differential intensity equal to the measured intensity minus the intensity of another point of the first image shifted along the first transverse direction relative to said first point and shifted along the first direction relative to the line;

c3) constituting the first final image by superimposing the first differential lines established for all of the first images acquired during the second sequence;

in step c2), the other point is one of the first points of the line;

the method is defined as below:

b) during the first sequence, the second heat input element scans the second zone while occupying, at a plurality of successive moments, a plurality of successive positions, and the second photosensitive surface element acquires a plurality of second images of the infrared radiation emitted by the second zone at said plurality of moments;

d1) for each second image acquired during the first sequence, determining the given moment from the plurality of moments at which said second image was acquired and extracting, from said second image, a line of second points corresponding to the position of the second heat input element at a second given moment (ti2'), the line comprising a second upstream end point situated furthest along the second direction and a second downstream end point shifted relative to the first upstream end point opposite the second direction and along a second transverse direction perpendicular to second first direction, each second point having a measured intensity representative of the temperature of the surface of the part in a zone corresponding to said second point;

d2) establishing a second differential line by assigning each second point a differential intensity equal to the measured intensity minus the intensity of another point of the second image shifted along the second transverse direction relative to said second point and shifted along the second direction relative to the line;

d3) constituting the second final image by superimposing the second differential lines established for all of the second images acquired during the first sequence;

in step d2), the other point is one of the second points of the line;

the second given moment is equal to the given moment plus a predetermined time shift;

the part is immobile during each sequence.

According to a second aspect, the invention provides a photothermal examination unit for a part, said unit comprising:

- a first scanning device for scanning a first zone of a surface of the part with a first heat input element, arranged to perform the scanning along a plurality of lines substantially parallel to a first direction;
- an acquisition device comprising a first photosensitive surface element arranged to acquire images of the infrared radiation emitted by said first zone;
- a second scanning device for scanning a second zone of the surface of the part with a second heat input element, arranged to perform the scanning along a plurality of lines substantially parallel to a second direction;
- the acquisition device having a second photosensitive surface element arranged to acquire images of the infrared radiation emitted by said second zone;
- the first and second scanning devices being arranged to scan the first and second zones simultaneously, the first and second photosensitive surface elements being separate from one another;
- the second direction forms a first non-zero angle with the first direction, said first angle preferably being larger than 30°, or
- the second direction is substantially parallel to the first direction, the first and second heat input elements being lines forming a second non-zero angle between them, said second angle preferably being larger than 30°.

The unit may further have one or more of the features below, considered individually or according to any technical possible combination(s):

- the unit is such that:
  - the first scanning device is able to scan the second zone of the surface of the part with the first heat input element, and to perform the scanning along a plurality of lines substantially parallel to the first direction;
  - the first photosensitive surface element is able to acquire images of the infrared radiation emitted by said second zone;
  - the second scanning device is able to scan a third zone of the surface of the part with the first heat input element, and to perform the scanning along a plurality of lines substantially parallel to the second direction;
  - the second photosensitive surface element is able to acquire images of the infrared radiation emitted by said third zone;
- the first and second scanning devices being arranged to scan the second and third zones simultaneously;
- the unit comprises a computer programmed to carry out:
  - a first processing step, in which first and/or second final images of the second zone are calculated respectively from images of the infrared radiation emitted by said second zone and respectively collected by the first and/or second photosensitive surface elements, respectively during the first and/or second sequences;
  - a second processing step, in which any structural defects in the second zone are detected by using the first and/or second final images obtained in the first processing step;
- the unit is such that:
  - a) the first scanning device is arranged so that the first heat input element scans the second zone while occupying, at a plurality of successive moments, a plurality of successive positions, and the acquisition device is programmed so that the first photosensitive surface element acquires a plurality of images of the infrared radiation emitted by the second zone at said plurality of moments; and/or
  - b) the second scanning device is arranged so that the second heat input element scans the second zone while occupying, at a plurality of successive moments, a plurality of successive positions, and the acquisition device is programmed so that the second photosensitive surface element acquires a plurality of images of the infrared radiation emitted by the second zone at said plurality of moments;
- the computer being programmed to carry out the following operations during the first processing step:
  - c) for each image acquired by the first photosensitive surface element, determining the given moment from the plurality of moments at which that image was acquired and extracting, from said image, a plurality of first points corresponding to the position of the first heat input element at a second given moment, the second given moment being equal to the given moment plus a predetermined time shift; constituting the first final image by superimposing the first point extracted from all of the images acquired by the first photosensitive surface element; and/or
  - c) for each image acquired by the second photosensitive surface element, determining the given moment from the plurality of moments at which that image was acquired and extracting, from said image, a plurality of second points corresponding to the position of the second heat input element at a second given moment, the second given moment being equal to the given moment plus a predetermined time shift; constituting the second final image by superimposing the second points extracted from all of the images acquired by the second photosensitive surface element;
  - the second direction is substantially parallel to the first direction, the first heat input element being a line forming, with the first direction, an angle comprised between 20° and 70°, the second heat input element being a line forming, with the second direction, an angle comprised between 110° and 160°;
- the method is such that:
  - a) the first scanning device is arranged so that the first heat input element scans the second zone while occupying, at a plurality of successive moments, a plurality of successive positions, and the acquisition device is programmed so that the first photosensitive surface element acquires a plurality of first images of the infrared radiation emitted by the second zone at said plurality of moments;
- and the computer is programmed to carry out the following operations during the first processing step:
  - c1) for each first image acquired by the first photosensitive surface element, determining the given moment from the plurality of moments at which said first image was acquired and extracting, from said first image, a line of first points corresponding to the position of the first heat input element at a second given moment, the line comprising a first upstream end point situated furthest along the first direction and a first downstream end point shifted relative to the first upstream end point opposite the first direction and along a first transverse direction perpendicular to the first direction, each first point having a measured intensity representative of the temperature of the surface of the part in a zone corresponding to said first point;
  - c2) establishing a first differential line by assigning each first point a differential intensity equal to the measured intensity minus the intensity of another point of the first image shifted along the first transverse direction relative to said first point and shifted along the first direction relative to the line;

c3) constituting the first final image by superimposing the first differential lines established for all of the first images acquired by the first photosensitive surface element;

in step c2), the other point is one of the first points of the line;

the method is such that:

b) the second scanning device is arranged so that the second heat input element scans the second zone while occupying, at a plurality of successive moments, a plurality of successive positions, and the acquisition device is programmed so that the second photosensitive surface element acquires a plurality of second images of the infrared radiation emitted by the second zone at said plurality of moments;

and the computer is programmed to carry out the following operations during the first processing step:

d1) for each second image acquired by the second photosensitive surface element, determining the given moment from the plurality of moments at which said second image was acquired and extracting, from said second image, a line of second points corresponding to the position of the second heat input element at a second given moment, the line comprising a second upstream end point situated furthest along the second direction and a second downstream end point shifted relative to the second upstream end point opposite the second direction and along a second transverse direction perpendicular to second first direction, each second point having a measured intensity representative of the temperature of the surface of the part in a zone corresponding to said second point;

d2) establishing a second differential line by assigning each second point a differential intensity equal to the measured intensity minus the value of another point of the second image shifted along the second transverse direction relative to said second point and shifted along the second direction relative to the line;

d3) constituting the second final image by superimposing the second differential lines established for all of the second images acquired during the second sequence;

in step d2), the other point is one of the second points of the line;

the second given moment is equal to the given moment plus a predetermined time shift.

BRIEF SUMMARY OF THE DRAWINGS

Other features and advantages of the invention will emerge from the following detailed description, provided for information and non-limitingly, in reference to the appended figures, in which.

DETAILED DESCRIPTION

Figure 1:
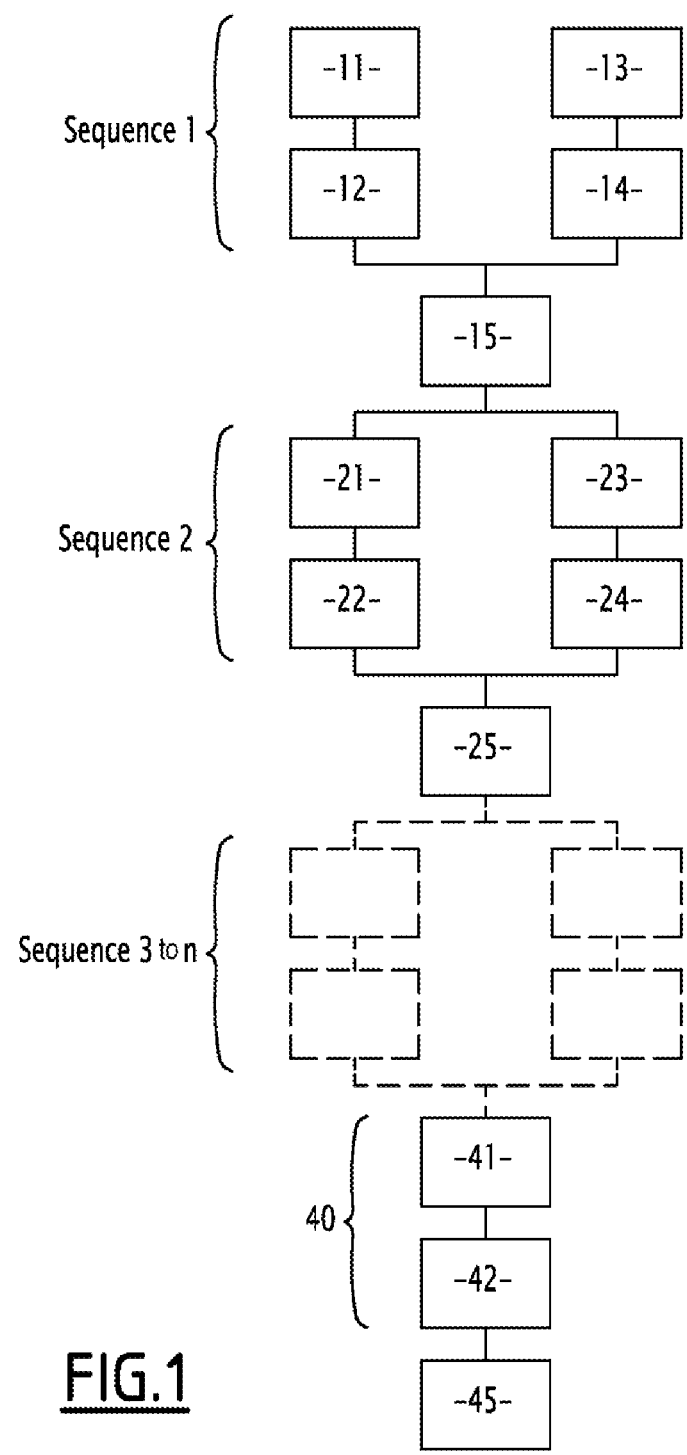
FIG. 1 is a diagram of steps of a first embodiment of the method according to the invention.

The method whereof the steps are shown in FIG. 1 is an examination method of the active photothermal type. The method is said to be active because the part to be characterized undergoes heating. The method is said to be photothermal because it is based on the acquisition of infrared images of the heated part.

This method is particularly suitable for detecting blocking or non-blocking defects in industrial components. It is particularly suitable for metal parts, in particular metal components of nuclear power plants.

The examination method is intended to perform the mechanized, automated or robotic inspection of such parts, during manufacturing or maintenance.

Figure 2:
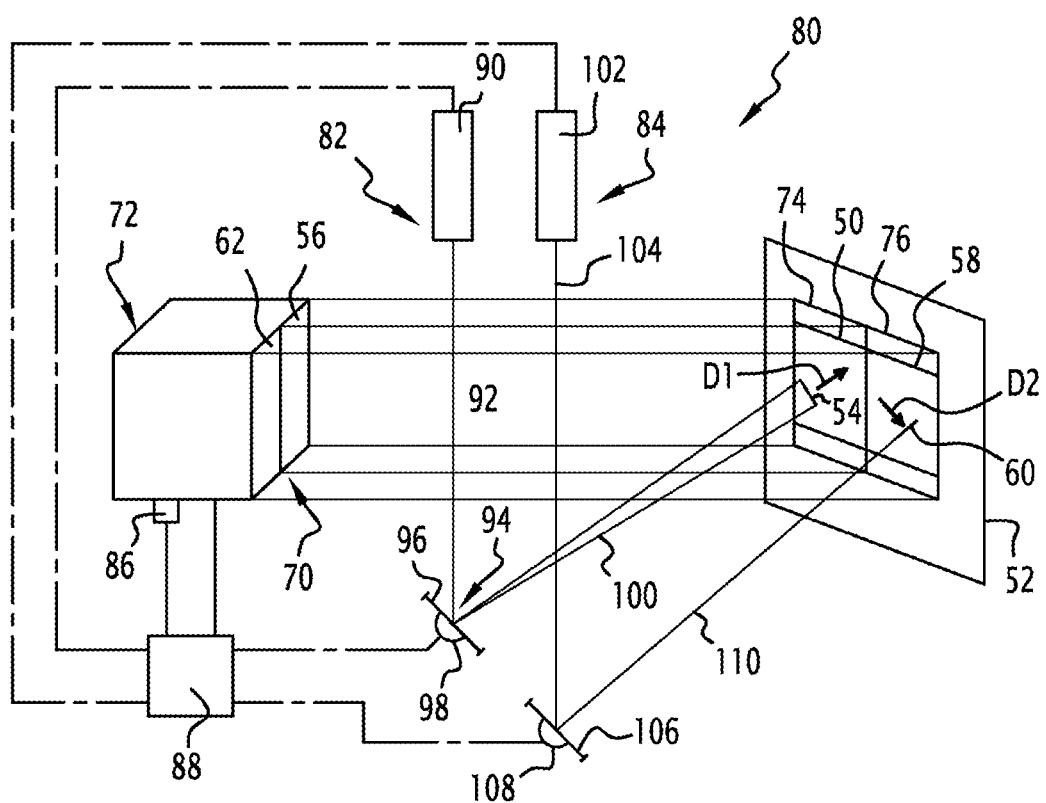
FIG. 2 is a simplified diagrammatic illustration of a photothermal examination unit according to an embodiment of the invention.

A first embodiment is illustrated in FIGS. 1 and 2. The method further comprises a first sequence having the following steps:

step 11: scanning a first zone 50 of the surface 52 of the part to be examined, with a first heat input element 54, the scanning being done along a plurality of lines substantially parallel to a first direction (D1 in FIG. 2);

step 12: acquiring images of the infrared radiation emitted by said first zone 50 using a first photosensitive surface element 56;

step 13: scanning a second zone 58 of the surface 52 with a second heat input element 60, the scanning being done along a plurality of lines substantially parallel to a second direction (D2 in FIG. 2) forming a non-zero angle $\alpha$ with the first direction;

step 14: acquiring images of the infrared radiation emitted by said second zones 58 using a second photosensitive surface element 62.

During the first sequence, the first and second zones 50 and 58 are scanned simultaneously. The acquisition of the images of the infrared radiation emitted by the first and second zones 50, 58, using first and second photosensitive surface elements 56, 62 is also simultaneous.

The method typically includes one or several other sequences similar to the first sequence, making it possible to acquire images of the entire surface of the part. These additional sequences are done with an overlap, such that each zone of the surface is scanned during a sequence with the first heat input element along lines substantially parallel to the first direction with acquisition of images by the first photosensitive surface element, then, during another sequence, scanned by the second heat input element, along a plurality of lines parallel to the second direction, with images being acquired by the second photosensitive surface element.

The part is immobile during each sequence, in particular relative to the means allowing the acquisition of images of the infrared radiation.

The scanning order is unimportant. Each zone may first be scanned by the first heat input element, then by the second, or conversely first by the second heat input element, then by the first.

Figure 3:
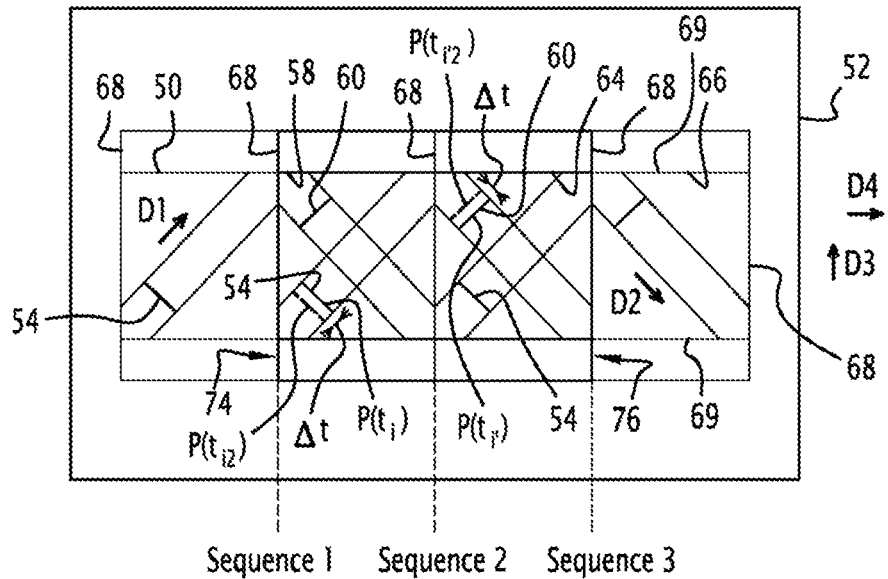
FIG. 3 is a developed view of the surface of the part to be examined, showing the object fields during three successive measuring sequences for the first embodiment.

More specifically, the method further comprises at least one second sequence having the following steps, as illustrated in FIGS. 1 and 3:

step 21: scanning the second zone 60 of the surface 52 of the part with the first heat input element 54, the scanning being done along a plurality of lines substantially parallel to the first direction D1;

step 22: acquiring the images of the infrared radiation emitted by said second zone 60 using the first photosensitive surface element 56;

step 23: scanning a third zone 64 of the surface 52 of the part with the second heat input element 60, the scanning being done along a plurality of lines substantially parallel to the second direction D2;

step 24: acquiring the images of the infrared radiation emitted by said third zone 64 using the second photosensitive surface element 62.

During the second sequence, the second and third zones 60, 64 are scanned simultaneously. The infrared radiation emitted by the second and third zones are acquired by the first and second photosensitive surface elements 56, 62 simultaneously.

The method comprises, between the first sequence and the second sequence, a step 15 for moving the first and second photosensitive surface elements 56, 62 relative to the part.

During the first sequence, the first and second photosensitive surface elements 56, 62 occupy a first position in which the first and second photosensitive surface elements 56, 62 are arranged so as to receive the infrared radiation respectively emitted by the first zone 50 and by the second zone 58 of the surface 52. The photosensitive surface elements 56, 62 are moved during step 15 to a second position, in which the first and second photosensitive surface elements 56, 62 are arranged so as to receive the infrared radiation respectively emitted by the second zone 58 and by the third zone 64.

As illustrated in FIG. 3, the method for example includes a third sequence identical to the first and second sequences, during which the third zone 64 is scanned by the first heat input element 54, with scanning along a plurality of lines substantially parallel to the first direction D1, and the first photosensitive surface element 56 acquires images of the infrared radiation emitted by said third zone 64. Simultaneously, a fourth zone 66 of the surface 52 is scanned by the second heat input element 60, along a plurality of lines substantially parallel to the second direction D2, and infrared radiation images emitted by the fourth zone are acquired using the second photosensitive surface element 62. Between the second sequence and the third sequence, the method of course includes a step 25 for moving the first and second photosensitive surface elements 56, 62, to place these photosensitive surface elements 56, 62 in positions where they can respectively capture the infrared radiation of the third zone 64 and the infrared radiation of the fourth zone 66.

In the example shown in the figures, the first and second zones 50, 58 of the surface 52 of the part, which are scanned simultaneously, are contiguous. Likewise, the second and third zones 58 and 64 are contiguous. Thus, in each sequence, the zones of the surface of the part that are scanned simultaneously are contiguous.

Alternatively, these zones are not contiguous, and are separated from one another.

The angle α between the first and second directions is preferably comprised between 45° and 135°, more preferably comprised between 60° and 120°. Typically, said angle α is close or equal to 90°. It is in particular chosen based on the curve of the zone of the part that must be scanned.

The first and second heat input elements 54, 60 are obtained using a laser with a defined geometric shape, a continuous or pulsed emission bulb, an inductive winding, etc. Alternatively, the first and second heat input elements 54, 60 are of any other type suitable for the function.

The laser creates, on the surface of the part, a heat input element that can have any type of shape. In the example shown in FIG. 2, the first and second heat input elements 54, 60 are elongated segments along directions perpendicular to the movement direction of the heat input element. Typically, the first and second heat input elements are in this case projected over the surface of the part in the form of a segment. Alternatively, the first and second heat input elements 54, 60 are projected over the surface of the part in the form of a point, this point being moved at a high speed so as to constitute a heat input element in the form of a segment.

The laser can also create a heat input element having the form of a circle, an ellipse, a rectangle, or any other suitable shape.

In one example embodiment, the segment has a length comprised between 10 and 30 mm. It has a thickness comprised between 1 to 3 mm.

In the example embodiment shown in the figures, each zone 50, 58, 64, 66 of the surface 52 is in the shape of a square. As shown in FIG. 3, these zones are defined by first edges 68, parallel to one another and parallel to a third direction D3. They are also defined by two edges 69, perpendicular to the edges 68 and therefore extending along a fourth direction D4. The first and second directions D1, D2 form an angle in the illustrated example of 45° relative to the directions D3 and D4. Alternatively, the zones 50, 58, 64, 66 of the par are not in the shape of a square, but have any other shape. The first and second directions can also form another angle relative to the directions D3 and D4, different from 45°.

Typically, as shown in FIG. 2, the first and second photosensitive surface elements 56, 62 are two parts of a same photosensitive surface 70 of a matricial sensor 72. This sensor is typically a digital infrared camera. Alternatively, the first and second photosensitive surface elements 56, 62 are not part of the same photosensitive surface. These are for example the photosensitive surfaces of two linear digital infrared cameras that are separate from and independent of one another.

In each sequence, the first photosensitive surface element 56 acquires images of the infrared radiation emitted by a first object field 74 containing a zone to be inspected. The second photosensitive surface element 62 acquires images of the infrared radiation emitted by a second object field 76 containing another zone to be inspected.

Thus, during the first sequence, the first object field 74 contains the first zone 50, and the second object field 76 contains the second zone 58. During the second sequence, the first object field 74 contains the second zone 58, and the second object field 76 contains the third zone 64.

The first and second object fields 74, 76 are set during each sequence.

In the illustrated example, the object fields 74, 76 are slightly larger than the zones 50, 58, 64, 66. Here, they each have a rectangular shape, with a height along the third direction D3 slightly larger than that of the zones 50, 58, 64, 66. Conversely, along the fourth direction D4, they have the same width as the zones 50, 58, 64, 66.

Alternatively, the first and second object fields 74, 76 have exactly the same shape as the zones to be inspected. According to another alternative, the first and second object fields have any other appropriate circular, oval, etc. shape.

During each sequence, the first photosensitive surface element 56 acquires images of the infrared radiation emitted at least by the entire zone to be inspected. More specifically, the first photosensitive surface element 56 acquires infrared radiation images emitted by the entire first object field 74. Alternatively, the first photosensitive surface element 56 acquires images of the infrared radiation emitted at least by only a fraction of the inspected zone.

Likewise, during each sequence, the second photosensitive surface element 62 acquires infrared radiation images emitted by the entire second zone 58, and typically emitted by the entire second object field 76. Alternatively, the second photosensitive surface element 62 acquires images of only a fraction of the inspected zone.

As shown in FIG. 1, the method further comprises, after the different sequences described above:

- a first processing step 40, in which first and/or second final images of each zone are calculated from images of the infrared radiation emitted by each zone and respectively collected by the first and/or second photosensitive surface elements 56, 62 during the different scanning sequences;
- a second processing step 45, in which any structural defects in the zone are detected by using the first and/or second final images obtained in the first processing step 40.

Thus, during the first processing step 40, first and/or second final images of the second zone 58 are respectively calculated from images acquired by the first and/or second photosensitive surface elements 56, 62, during the second and/or first sequences. For the third zone 64, the first and/or second final images are calculated from images respectively collected by the first and/or second photosensitive surface elements 56, 62 during the third and second sequences.

Preferably, the first and second final images of each zone are calculated in the first processing step 40. This allows much more reliable detection of structural defects during the second processing step 45. However, it is possible to consider calculating only the first or second final image, and only using a single final image to determine the presence of a defect.

The first processing step 40 will now be outlined, for the second zone 58. The first processing step is identical for the other zones of the surface 52.

It will first be noted that, during the second sequence, the first heat input element 54 scans the second zone 58 while occupying, at a plurality of successive moments ti, a plurality of successive positions P(ti). The first photosensitive surface element 56 acquires a plurality of images I(ti) of the infrared radiation emitted by the second zone 58 at the plurality of moments ti.

Likewise, during the first sequence, the second heat input element 60 scans the second zone 58 while occupying, at a plurality of successive moments ti', a plurality of successive positions P(ti'). The second photosensitive surface element 62 acquires a plurality of images I(ti') of the infrared radiation emitted by the second zone 58 at said plurality of moments ti'.

Figure 4:
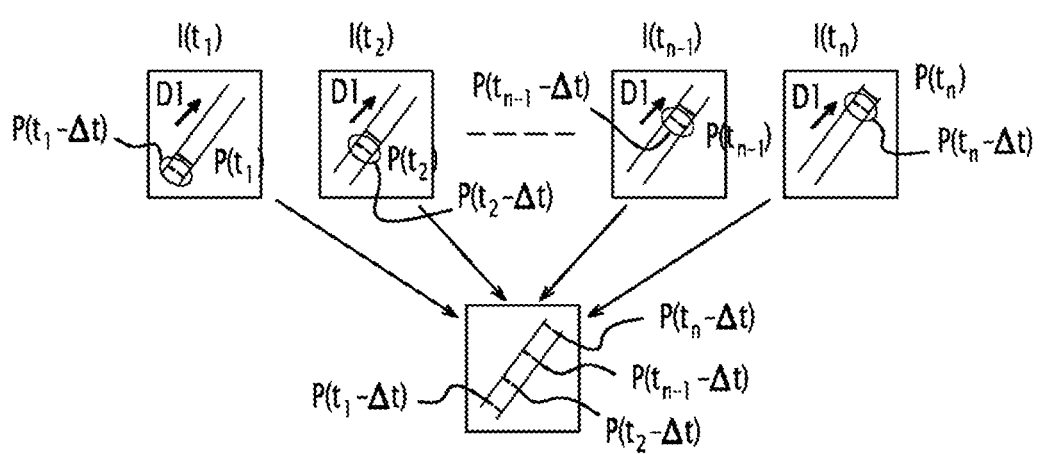
FIG. 4 is a diagrammatic illustration of the first processing step of the first embodiment, making it possible to constitute a final image of a zone, from acquired images.

The first processing step 40 comprises a first sub-step 41, during which the following operations are done, as illustrated in FIG. 4:

- for each image I(ti) acquired during the second sequence, determining the given moment ti from the plurality of moments at which said image I(ti) was acquired;
- extracting, from said image I(ti), a plurality of first points corresponding to the position P(ti2) of the first heat input element 54 at a second given moment $ti_2$, the second given moment $ti_2$ being equal to the given moment ti plus a predetermined time shift;
- constituting the first final image by superimposing the first points extracted from all of the images I(ti) acquired during the second sequence.

The first processing step 40 further preferably comprises a second sub-step 42, during which the following operations are done:

- for each image I(ti') acquired during the first sequence, determining the given moment ti from the plurality of moments at which said image I(ti') was acquired;
- extracting, from said image I(ti'), a plurality of second points corresponding to the position of the second heat input element 60 at a second given moment ti2', the second given moment ti2' being equal to the given moment ti' plus a predetermined time shift ΔT';
- constituting the second final image by superimposing the second points extracted from all of the images I(ti') acquired during the first sequence.

These operations are shown diagrammatically in FIG. 4, for the establishment of the first final image.

For the other zones of the surface of the part, the first processing step is similar. However, the images acquired from other sequences are used. For example, for the third zone 64, the images of the infrared radiation emitted by the third zone 64 during the third sequence are used to establish the first final image. The images acquired during the second sequence are used to establish the second final image.

The predetermined time shift ΔT, ΔT' is constant for the processing of all of the images acquired during a same sequence. Generally, it is chosen such that ΔT=ΔT'. Alternatively, ΔT is different from ΔT'.

The same time shift is generally chosen to process images from the different sequences.

This shift may be zero, positive or negative, as explained in WO 98/39640.

Because the first and second heat input elements 54, 58 scan the entirety of each zone, the first and second points extracted from the acquired images 60 will cover substantially the entire zone. Final images are thus reconstituted covering the entirety of each zone.

The first points extracted from each acquired image strictly cover the expanse of the first heat input element 54 at the second given moment ti'2. Alternatively, the first points cover an expanse slightly larger or slightly smaller than that of the first heat input element at the second given moment ti2. Likewise, the second points strictly cover the expanse of the second heat input element 60 at the second given moment ti'2. Alternatively, they cover an expanse slightly larger or slightly smaller than that of the second heat input element 60.

The first processing step 40 is done by calculation.

During the second processing step 45, any structural defects in each zone are identified by detecting whether heat concentrations exist in the first and/or second final images. Thus, in case of blocking or non-blocking defect in the zone, the heat energy contributed by the first or second heat input element cannot spread (in whole or in part) beyond the defect, and therefore accumulates (in whole or in part) on the edge of the defect.

This second processing step is done by calculation, using algorithms of a known type.

FIG. 2 shows the unit 80 provided for the photothermal examination of a part. The unit 80 is provided to carry out the photothermal examination method according to an embodiment of the invention, described above.

The unit 80 comprises:

- a first scanning device 82, for scanning the first zone 50 of the surface 52 with the first heat input element 54, the first scanning device 82 being arranged to perform the scanning along a plurality of lines substantially parallel to the first direction D1;

an acquisition device (infrared camera 72 in the illustrated example), comprising the first photosensitive surface element 56, this first photosensitive surface element 56 being arranged to acquire images of the infrared radiation emitted by the first zone 50;

a second scanning device 84, for scanning the second zone 58 of the surface 52 with the second heat input element 60, this second scanning device 84 being arranged to perform the scanning along a plurality of lines substantially parallel to the second direction D2;

the second photosensitive surface element 62 being part of the acquisition device and being arranged to acquire images of the infrared radiation emitted by the second zone 58.

The first and second scanning devices 82, 84 are arranged to scan the first and second zones simultaneously. The first and second photosensitive surface elements 56, 62, as indicated above, are separate from one another. They are arranged to be able to simultaneously acquire images of the infrared radiation emitted by the first and second zones 50, 58.

The unit 80 further includes a device 86 provided to move the first and second photosensitive surface elements 56, 62 relative to the part to be examined and a computer 88.

The first scanning device 82 is able not only to scan the first zone 50, but also the second zone 58 and all of the other zones of the surface 52 with the first heat input element 54, along a plurality of lines substantially parallel to the first direction D1.

To that end, in the illustrated example, it includes a laser source 90, provided to emit a laser beam 92, and a goniometer 94 suitable for reflecting the laser beam 92 toward the surface 52. The goniometer 94 includes a reflective surface 96 and a device 98 provided to adjust the orientation of the reflective surface 96. The device 98 is driven by the computer 88. Alternatively, the goniometer 94 is replaced by a mirror or any other suitable device.

The laser beam 92 is reflected by the surface 96 and forms a reflected beam 100 that creates the first heat input element 54 on the surface 52.

The computer 88 is programmed to control the orientation device 98 so as to cause, during each scanning sequence, the movement of the first heat input element 54 along a plurality of lines substantially parallel to the direction D1, so as to scan the entire zone to be examined. The computer 88 is also programmed to modify, between two sequences, the orientation of the surface 96 such that the first heat input element is moved to the zone that will be scanned during the following sequence.

The second scanning device 84 is typically similar to the first. In the illustrated example, it includes a laser source 102 provided to emit a laser beam 104, and an orientation device 105. The orientation device 105 includes a reflective surface 106 and an orientation member 108 making it possible to modify the orientation of the reflective surface 106. Orientation member 108 is driven by the computer 88. The laser beam 104 is reflected by the reflective member 106 and forms a reflected beam 110 that creates the second heat input element 60 on the surface 52. The computer 88 is programmed to control, during each sequence, the orientation device 108 so as to ensure complete scanning of the zone to be examined, along a plurality of lines substantially parallel to the second direction D2. It is also programmed to move, between two sequences, the second heat input element to the zone needing to be examined in the following sequence.

In the illustrated example, the first and second photosensitive surface elements 56, 62 are two juxtaposed zones of the matricial photosensitive surface 70 of a digital infrared camera 72.

The acquisition device 72 is programmed so that the first photosensitive surface element 56 acquires a plurality of images I(ti) at a plurality of moments ti, for example images of the second zone 58 or any other zone.

The acquisition device 72 is also programmed so that the second photosensitive surface element 62 acquires a plurality of images I(ti') at a plurality of moments ti', for example images of the second zone 58 or any other zone.

The device 86 is provided to move the photosensitive surface elements 56, 62 relative to the part, between the sequences.

Thus, during the first sequence, the first and second photosensitive surface elements are in first respective positions chosen so as to receive the infrared radiation respectively emitted by the first zone 50 and by the second zone 58. During the second sequence, the first and second photosensitive surface elements 56 and 62 are in second respective positions allowing them to receive the infrared radiation respectively emitted by the second zone 58 and by the third zone 58. During the other sequences, the first and second photosensitive surface elements 56 and 62 are in still other positions allowing them to each receive the infrared radiation emitted by one of the zones of the surface 62. The device 86 is arranged to move the acquisition device so as to transfer the first and second photosensitive surface elements from one position to another.

The device 86 is driven by the computer 88.

The device 86 is for example a rail or a ball joint, or any other suitable mechanical device.

Alternatively, the first and second photosensitive surface elements 56 and 62 are fixed. Conversely, the acquisition device includes one or several movable members suitable for reflecting the infrared radiation from the zones of the surface 52 to the first and second photosensitive surface elements 56, 62. This reflection device is placed between each sequence, and arranged in a position chosen to reflect the infrared radiation from the required zones toward the first and second photosensitive surface elements.

The reflection device is driven by the computer 88.

Furthermore, the computer is programmed to carry out the first processing step 40 and the second processing step 45 described above.

A second embodiment of the invention will now be described in reference to FIGS. 5 to 9. Only the differences between the second embodiment and the first will be outlined below. Identical elements or elements performing the same function in the two embodiments will be designated using the same references.

In the second embodiment, the first and second heat input elements 54 and 60 are lines forming a second non-zero angle β between them.

The second angle β [is] preferably greater than 30°, also preferably comprised between 45° and 135°, and typically comprised between 60° and 120°. Typically, the median direction I between the two lines is parallel (or substantially parallel) to the first and second directions D1 and D2 (see FIG. 7).

The second direction D2 is substantially parallel to the first direction D1. This means that the first and second directions form an angle between them smaller than 10°, preferably smaller than 5°, and ideally equal to 0 (particularly in the case of planar surfaces).

Figure 7:
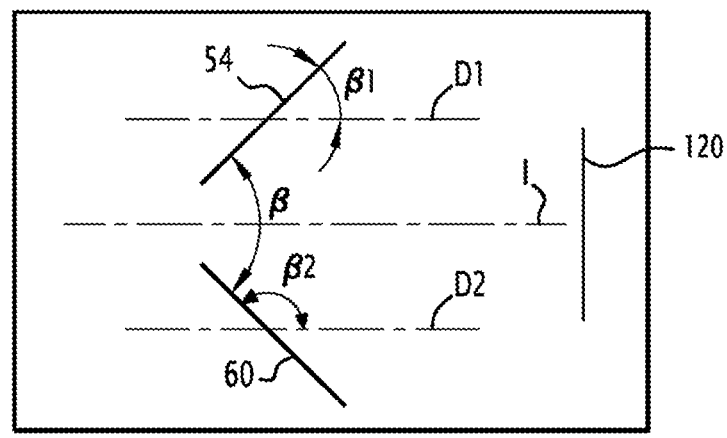
FIG. 7 illustrates the position of a defect of type A.

As shown in FIG. 7 for example, the first heat input element 54 is a line forming an angle β1 with the first direction D1 comprised between 20° and 70°, preferably comprised between 30° and 60°, and typically equal to 45°. The second heat input element 60 is a line forming an angle β2 with the second direction D2 comprised between 110° and 160°, preferably comprised between 120° and 150°, and typically equal to 135°. The angles β, β1 and β2 are specified here in the trigonometric direction.

The second embodiment implements the same scanning and image acquisition sequences 1 to n as the first embodiment, with the same steps in each sequence. Relative to the first embodiment, the only difference lies in the fact that the directions D1 and D2 are substantially parallel to one another for the second embodiment, whereas they are inclined relative to one another in the first embodiment. The scanning and image acquisition sequences 1 to n are separated by movement steps 15, 25, etc., identical to those of the first embodiment.

The first processing step 40 of the second embodiment is, however, different from that of the first embodiment.

Figure 5:
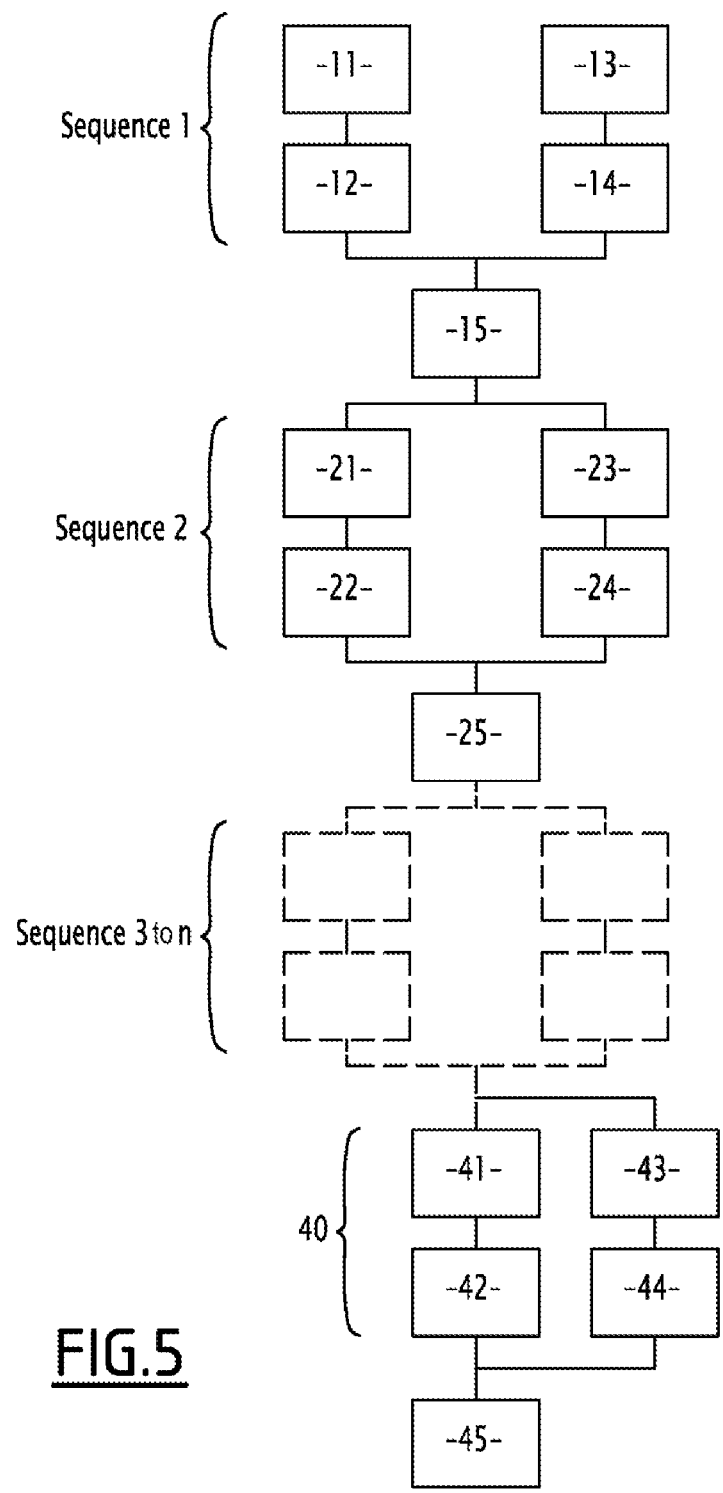
FIG. 5 is a diagram of steps of a second embodiment of the method according to the invention.
Figure 6:
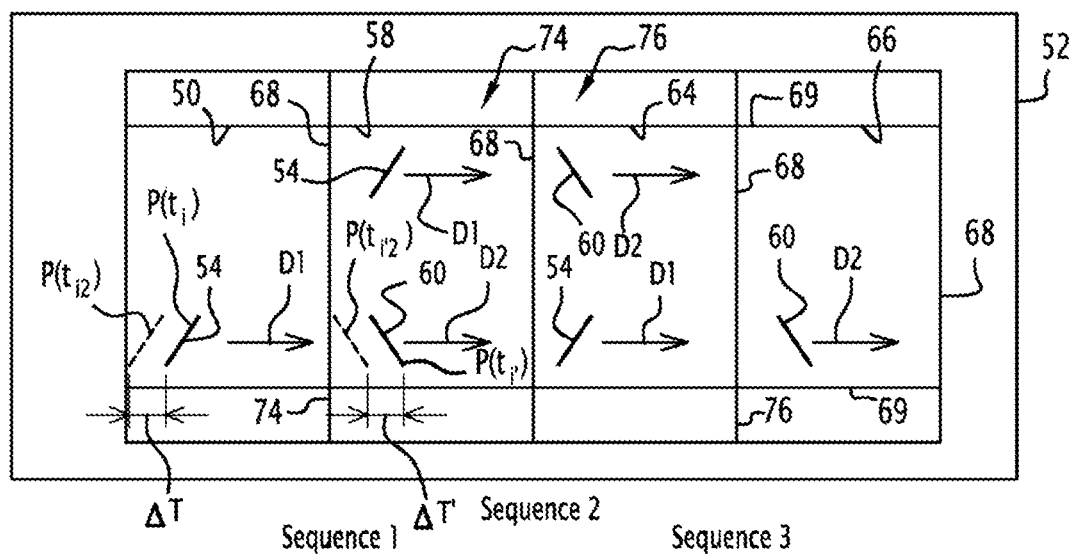
FIG. 6 is a view similar to that of FIG. 3, for the second embodiment of the invention.

In step 40, as shown in FIG. 5, two different processing operations are applied, on the same images.

The first processing operation seeks to identify the defects 120 that are substantially perpendicular to the movement direction of the first and second heat input elements, i.e., the first and second directions D1 and D2 (see FIG. 7).

This first processing operation implements first and second sub-steps 41 and 42, identical to those that are implemented in the first embodiment.

Figure 8:
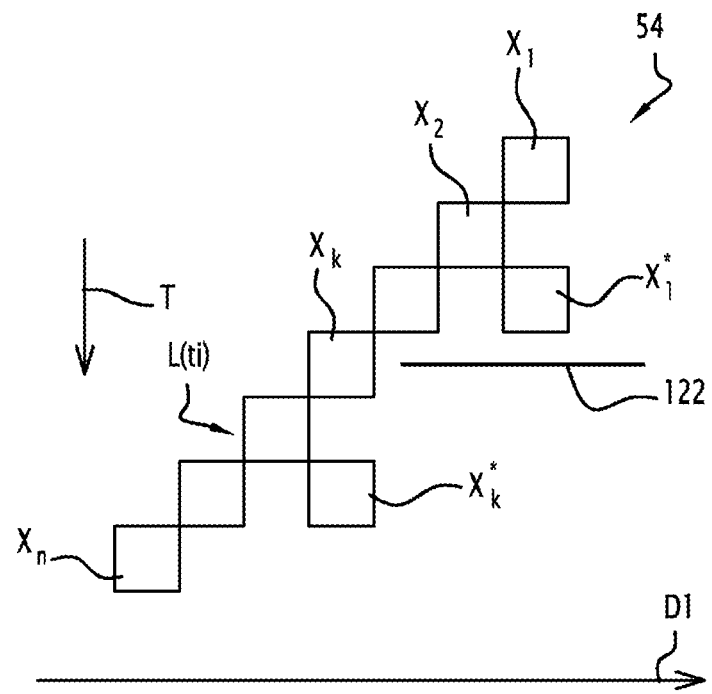
FIGS. 8 and 9 illustrate the position of a defect of type B and the corresponding digital processing strategy.
Figure 9:
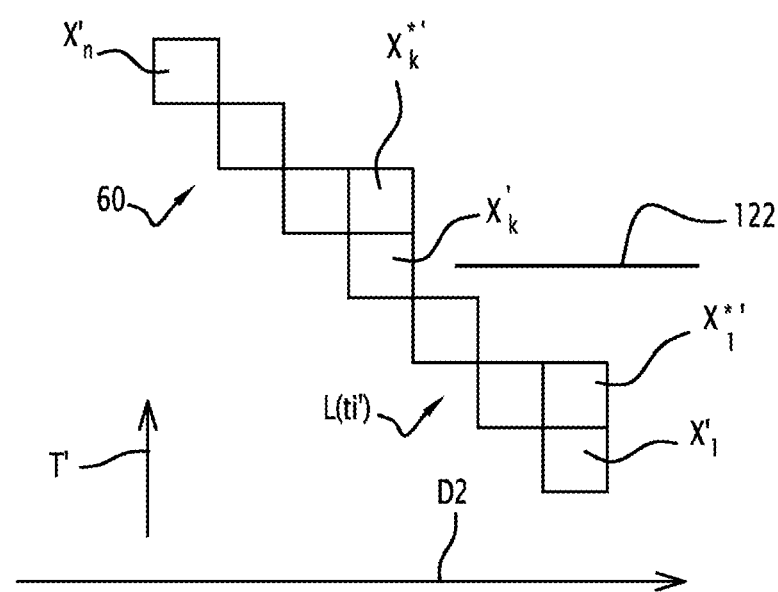

The second processing operation seeks to identify the defects 122 that are substantially parallel to the movement direction of the first and second heat input elements, i.e., the first and second directions D1 and D2 (see FIGS. 8 and 9).

This second processing operation will be described below for the second zone 58. The second processing step is identical for the other zones.

As for the first embodiment, during the second sequence, the first heat input element 54 scans the second zone 58 while occupying, at a plurality of successive moments ti, a plurality of successive positions P(ti). The first photosensitive surface element 56 acquires a plurality of first images I(ti) of the infrared radiation emitted by the second zone 58 at said plurality of moments ti.

Likewise, during the first sequence, the second heat input element 60 scans the second zone 58 while occupying, at a plurality of successive moments ti, a plurality of successive positions P(ti). The second photosensitive surface element 62 acquires a plurality of second images I(ti') of the infrared radiation emitted by the second zone 58 at said plurality of moments ti'.

The first processing step 40 comprises a first sub-step 43, during which the following operations are done.

For each first image I(ti) acquired during the second sequence, one first determines the given moment ti from the plurality of moments at which said first image I(ti) has been acquired and one extracts, from said first image I(ti), a line L(ti) of first points Xk corresponding to the position P(ti2) of the first heat input element 54 at a second given moment ti2.

Each point typically corresponds to a pixel, or a group of pixels.

The second given moment ti2 is equal to the given moment ti plus a predetermined time shift ΔT, as explained in reference to the first embodiment. ΔT is typically zero, or negative.

As shown in FIG. 8, the line L(ti) comprises a first upstream end point X1 situated furthest away along a first direction D1 and a first downstream end point Xn shifted relative to the first upstream endpoint X1 opposite the first direction D1. Because the first heat input element 54 is an inclined line relative to the first direction D1, the first downstream end point Xn is also shifted along the first transverse direction T perpendicular to the first direction D1.

The other first points Xk are juxtaposed next to one another in a line going from X1 to Xn.

Each first point Xk has a measured intensity, representative of the temperature of the surface 52 of the part in the zone corresponding to said point.

A first differential line is next established by assigning each first point Xk a differential intensity equal to the measured intensity minus the intensity of another point Xk* of the first image I(t) (see FIG. 8). The point Xk* is shifted along the first transverse direction T relative to said first point Xk and shifted along the first direction D1 relative to the line L(ti).

Shifted along the first direction D1 relative to the line L(ti) here means that the other point Xk* is on the line L(ti) or upstream from the line L(ti), i.e., in a zone that has not yet been traversed by the line L(ti).

The shift between Xk and Xk* is the same for all of the first points Xk, along the first direction and along the first transverse direction.

According to a first alternative, the other point Xk* is one of the first points Xk of the line L(ti). For example, Xk* is the point adjacent to Xk on the side of the downstream end point Xn. Alternatively, Xk* is separated from the first point Xk by a point of the line, or two points of the line, or more than two points of the line.

According to a second alternative, Xk* does not belong to the line. In the illustrated example, in FIG. 8, Xk* is shifted by zero pixels in the first direction D1 and by two pixels in the first transverse direction T.

Xk* is typically shifted relative to Xk by a strictly positive number of pixels in the first transverse direction, in particular to remain upstream from the line L(ti). Alternatively, Xk* is shifted relative to Xk by a strictly negative number of pixels in the first transverse direction, to remain downstream from the line L(ti).

Next, one constitutes the first final image by superimposing the first differential lines established for all of the first images I(ti) acquired during the second sequence;

The same operations are preferably done for the second images.

For each second image I(ti') acquired during the first sequence, one first determines the given moment ti' from the plurality of moments at which said second image I(ti') has been acquired and one extracts, from said second image I(ti'), a line L(ti) of second points L(ti') corresponding to the position P(ti2') of the second heat input element 60 at a second given moment ti2'.

Each point typically corresponds to a pixel, or a group of pixels.

The second given moment ti2' is equal to the given moment ti plus a predetermined time shift ΔT', as explained in reference to the first embodiment. ΔT is typically zero, or negative.

As shown in FIG. 9, the line comprising a second upstream end point X1' situated furthest away along the second direction D2 and a second downstream end point Xn' shifted relative to the second upstream endpoint X1' opposite the first direction D2. Because the second heat input element 60 is an inclined line relative to the second direction D2, the second downstream end point Xn' is shifted relative to the second upstream end point X1' along a second transverse direction T' perpendicular to the first second D1, which in FIG. 9 is the direction T' opposite the first transverse direction T.

The other second points Xk are juxtaposed next to one another in a line going from X1 to Xn.

Each second point Xk' has a measured intensity, representative of the temperature of the surface of the part 52 in the zone corresponding to said second point Xk'.

A second differential line is next established by assigning each second point Xk' a differential intensity equal to the measured intensity minus the intensity of another point Xk*' of the second image I(ti') (see FIG. 9). The other point Xk* is shifted along the second transverse direction T' relative to said second point Xk' and is shifted along the second direction D2 relative to the line L(ti').

Shifted along the second direction relative to the line L(ti') here means that the other point Xk*' is on the line L(ti') or upstream from the line L(ti'), i.e., in a zone that has not yet been traversed by the line L(ti').

The shift between Xk and Xk*' is the same for all of the second points Xk', along the second direction D2 and along the second transverse direction T'.

According to a first alternative, the other point Xk*' is one of the second points Xk' of the line L(ti'). For example, Xk* is the point adjacent to Xk' on the side of the downstream end point Xn'. Alternatively, Xk*' is separated from the first point Xk' by a point of the line, or two points of the line, or more than two points of the line.

According to a second alternative, Xk*' does not belong to the line. In the illustrated example, in FIG. 9, Xk*' is shifted by zero pixels in the first direction D2 and by one pixel in the second transverse direction T'.

Xk*' is shifted relative to Xk by a strictly positive number of pixels in the second transverse direction, in particular to remain upstream from the line L(ti'). Alternatively, Xk*' is shifted relative to Xk' by a strictly negative number of pixels in the second transverse direction, to remain downstream from the line L(ti').

Next, one constitutes the second final image by superimposing the second differential lines established for all of the second images I(ti') acquired during the first sequence.

In one non-preferred alternative, the operations described above are done only for the first images, or only for the second images.

During the second processing step 45, any structural defects substantially perpendicular to the first and second directions D1 and D2 are identified by examining the final images obtained using the first processing operation (sub-steps 41, 42). The defects are identified by detecting whether heat concentrations exist in the first and/or second final images. Thus, in case of blocking or non-blocking defect in the zone, the heat energy contributed by the first or second heat input element cannot spread (in whole or in part) beyond the defect, and therefore accumulates (in whole or in part) on the edge of the defect.

During the second processing step 45, any structural defects substantially parallel to the first and second directions D1 and D2 are identified by examining the final images obtained using the second processing operation (sub-steps 43, 44). These images show the temperature gradients in a direction substantially perpendicular to the movement direction. If a defect parallel to the movement direction is present, due to the incline of the lines formed by the heat input elements, the heat will accumulate more on one edge of the defect than on the opposite edge. In the example of FIG. 8, the heat will first accumulate on the edge of the defect 122 situated toward the top of FIG. 8, due to the closed angle between this edge and the line formed by the heat input element. Conversely, the heat will accumulate last on the edge situated toward the bottom of FIG. 8, due to the more open angle between this edge and the line formed by the heat input element. The situation is reversed in FIG. 9. A temperature gradient is thus created at the moment t perpendicular to the movement direction, on either side of the defect.

The structural defects, for example cracks, that are neither parallel nor perpendicular to the first and second directions D1 and D2 will be detected in the final images resulting from the first or second processing operation, based on their orientation.

This first and second processing steps are done by calculation, using algorithms of a known type.

The second embodiment is implemented with the same photothermal examination unit as the first embodiment, only the programming of the computer 88 being modified. The computer is programmed to carry out the method according to the second embodiment.

It should be noted that both embodiments of the invention have been described as being implemented with a fixed matricial sensor 72 during each scanning and image acquisition sequence. Alternatively, both embodiments of the invention are implemented with one or two mobile sensors, which scan the surface to be examined at the same time as the heat input elements.

What is claimed is:

1. A photothermal examination method of a part, the method comprising a first sequence having the following steps:
    step 11: scanning a first zone of a surface of the part with a first heat input element, the scanning being done along a plurality of lines substantially parallel to a first direction;
    step 12: acquiring an image of the infrared radiation emitted by said first zone using a first photosensitive surface element;
    step 13: scanning a second zone of the surface of the part with a second heat input element, the scanning being done along a plurality of lines substantially parallel to a second direction; and
    step 14: acquiring an image of the infrared radiation emitted by said second zone using a second photosensitive surface element;
    the first and second zones being scanned simultaneously and the first and second photosensitive surfaces being separate from one another;
    the second direction forming a first non-zero angle with the first direction, or the second direction being substantially parallel to the first direction, the first and second heat input elements being lines forming a second non-zero angle between them.

2. The method according to claim 1, wherein the first and second photosensitive surface elements are two parts of a same photosensitive surface of a matricial sensor.

3. The method according to claim 1, wherein the method further comprises at least one second sequence having the following steps:
    step 21: scanning the second zone of the surface of the part with the first heat input element, the scanning being done along a plurality of lines substantially parallel to the first direction;

step 22: acquiring an image of the infrared radiation emitted by said second zone using the first photosensitive surface element;

step 23: scanning a third zone of the surface of the part with the second heat input element, the scanning being done along a plurality of lines substantially parallel to the second direction; and step 24: acquiring an image of the infrared radiation emitted by said third zone using the second photosensitive surface element;

the second and third zones being scanned simultaneously.

4. The method according to claim 3 further comprising moving the first and second photosensitive surface elements relative to the part between the first sequence and the second sequence.

5. The method according to claim 3 further comprising, after the first and second sequence:

a first processing step, in which first and/or second final images of the second zone are calculated respectively from images of the infrared radiation emitted by said second zone and respectively collected by the first and/or second photosensitive surface elements, respectively during the second and/or first sequences; and a second processing step, in which any structural defects in the second zone are detected by using the first and/or second final images obtained in the first processing step.

6. The method according to claim 5, wherein:

a) during the second sequence, the first heat input element scans the second zone while occupying, at a plurality of successive moments, a plurality of successive positions, and the first photosensitive surface element acquires a plurality of images of the infrared radiation emitted by the second zone at said plurality of moments; and/or b) during the first sequence, the second heat input element scans the second zone while occupying, at a plurality of successive moments, a plurality of successive positions, and the second photosensitive surface element acquires a plurality of images of the infrared radiation emitted by the second zone at said plurality of moments;

the first processing step comprising the following operations:

c) for each image acquired during the second sequence, determining the given moment from the plurality of moments at which said image was acquired and extracting, from said image, a plurality of first points corresponding to the position of the first heat input element at a second given moment, the second given moment being equal to the given moment plus a predetermined time shift; constituting the first final image by superimposing the first point extracted from all of the images acquired during the second sequence; and/or d) for each image acquired during the first sequence, determining the given moment from the plurality of moments at which said image was acquired and extracting, from said image, a plurality of second points corresponding to the position of the second heat input element at a second given moment, the second given moment being equal to the given moment plus a predetermined time shift; constituting the second final image by superimposing the second point extracted from all of the images acquired during the first sequence.

7. The method according to claim 1, wherein, during the first sequence, the first photosensitive surface element acquires images of the infrared radiation emitted by a first object field containing the first zone, and the second photosensitive surface element acquires images of the infrared radiation emitted by a second object field containing the second zone, the first and second object fields being fixed during the first sequence.

8. The method according to claim 7, wherein during the first sequence, the first photosensitive surface element acquires images of the infrared radiation emitted by at least all of the first zone, and the second photosensitive surface element acquires images of the infrared radiation emitted by at least all of the second zone.

9. The method according to claim 1, wherein each zone of the surface of the part is scanned during a sequence with the first heat input element along a plurality of lines parallel to the first direction, and during another sequence with the second heat input element along a plurality of lines parallel to the second direction, images of the infrared radiation emitted by said zone being acquired by the first photosensitive surface element during said sequence and by the second photosensitive surface element during said other sequence.

10. The method according to claim 1, wherein the first and second heat input elements are generated by a laser with a defined geometric shape, or a continuous or pulsed emission bulb, or an inductive winding.

11. The method according to claim 1, wherein the second direction is substantially parallel to the first direction, the first heat input element being a line forming, with the first direction, an angle comprised between 20° and 70°, the second heat input element being a line forming, with the second direction, an angle comprised between 110° and 160°.

12. The method according to claim 11, further comprising, after the first and second sequence:

a first processing step, in which first and/or second final images of the second zone are calculated respectively from images of the infrared radiation emitted by said second zone and respectively collected by the first and/or second photosensitive surface elements, respectively during the second and/or first sequences;

a second processing step, in which any structural defects in the second zone are detected by using the first and/or second final images obtained in the first processing step; and wherein:

a) during the second sequence, the first heat input element scans the second zone while occupying, at a plurality of successive moments, a plurality of successive positions, and the first photosensitive surface element acquires a plurality of first images of the infrared radiation emitted by the second zone at said plurality of moments;

and wherein the first processing step comprises the following operations:

c1) for each first image acquired during the second sequence, determining the given moment from the plurality of moments at which said first image was acquired and extracting, from said first image, a line of first points corresponding to the position of the first heat input element at a second given moment, the line comprising a first upstream end point situated furthest along the first direction and a first downstream end point shifted relative to the first upstream end point opposite the first direction and along a first transverse direction perpendicular to the first direction, each first point having a measured intensity representative of the temperature of the surface of the part in a zone corresponding to said first point;

c2) establishing a first differential line by assigning each first point a differential intensity equal to the measured intensity minus the intensity of another point of the first image shifted along the first transverse direction relative to said first point and shifted along the first direction relative to the line; and c3) constituting the first final image by superimposing the first differential lines established for all of the first images acquired during the second sequence.

13. The method according to claim 12, wherein, in step c2), the other point is one of the first points of the line.

14. The method according to claim 12, further comprising, after the first and second sequence:

a first processing step, in which first and/or second final images of the second zone are calculated respectively from images of the infrared radiation emitted by said second zone and respectively collected by the first and/or second photosensitive surface elements, respectively during the second and/or first sequences;

a second processing step, in which any structural defects in the second zone are detected by using the first and/or second final images obtained in the first processing step; and wherein b) during the first sequence, the second heat input element scans the second zone while occupying, at a plurality of successive moments, a plurality of successive positions, and the second photosensitive surface element acquires a plurality of second images of the infrared radiation emitted by the second zone at said plurality of moments ;

d1) for each second image acquired during the first sequence, determining the given moment from the plurality of moments at which said second image was acquired and extracting, from said second image, a line of second points corresponding to the position of the second heat input element at a second given moment, the line comprising a second upstream end point situated furthest along the second direction and a second downstream end point shifted relative to the first upstream end point opposite the second direction and along a second transverse direction perpendicular to the second direction, each second point having a measured intensity representative of the temperature of the surface of the part in a zone corresponding to said second point;

d2) establishing a second differential line by assigning each second point a differential intensity equal to the measured intensity minus the intensity of another point of the second image shifted along the second transverse direction relative to said second point and shifted along the second direction relative to the line ;

d3) constituting the second final image by superimposing the second differential lines established for all of the second images acquired during the first sequence;

and wherein the second given moment is equal to the given moment plus a predetermined time shift, the second given moment being equal to the given moment plus a predetermined time shift.

15. The method according to claim 11, wherein it comprises, after the first and second sequence:

a first processing step, in which first and/or second final images of the second zone are calculated respectively from images of the infrared radiation emitted by said second zone and respectively collected by the first and/or second photosensitive surface elements, respectively during the second and/or first sequences;

a second processing step, in which any structural defects in the second zone are detected by using the first and/or second final images obtained in the first processing step; and wherein b) during the first sequence, the second heat input element scans the second zone while occupying, at a plurality of successive moments, a plurality of successive positions, and the second photosensitive surface element acquires a plurality of second images of the infrared radiation emitted by the second zone at said plurality of moments;

d1) for each second image acquired during the first sequence, determining the given moment from the plurality of moments at which said second image was acquired and extracting, from said second image, a line of second points corresponding to the position of the second heat input element at a second given moment, the line comprising a second upstream end point situated furthest along the second direction and a second downstream end point shifted relative to the first upstream end point opposite the second direction and along a second transverse direction perpendicular to the second direction, each second point having a measured intensity representative of the temperature of the surface of the part in a zone corresponding to said second point;

d2) establishing a second differential line by assigning each second point a differential intensity equal to the measured intensity minus the intensity of another point of the second image shifted along the second transverse direction relative to said second point and shifted along the second direction relative to the line;

d3) constituting the second final image by superimposing the second differential lines established for all of the second images acquired during the first sequence.

16. The method according to claim 15, wherein, in step d2), the other point is one of the first points of the line.

17. The method according to the claim 1, wherein the part is immobile during each sequence.

18. A photothermal examination unit for a part, said unit comprising:

a first scanner for scanning a first zone of a surface of the part with a first heat input element, arranged to perform the scanning along a plurality of lines substantially parallel to a first direction;

an acquirer comprising a first photosensitive surface element arranged to acquire images of the infrared radiation emitted by said first zone;

a second scanner for scanning a second zone of the surface of the part with a second heat input element, arranged to perform the scanning along a plurality of lines substantially parallel to a second direction;

the acquirer having a second photosensitive surface element arranged to acquire images of the infrared radiation emitted by said second zone;

the first and second scanners being arranged to scan the first and second zones simultaneously, the first and second photosensitive surface elements being separate from one another;

the second direction forming a first non-zero angle with the first direction, or the second direction being substantially parallel to the first direction, the first and second heat input elements being lines forming a second non-zero angle between them.

19. The unit according to claim 18, wherein
the first scanner is configured to scan the second zone of the surface of the part with the first heat input element, and to perform the scanning along a plurality of lines substantially parallel to the first direction;
the first photosensitive surface element is configured to acquire images of the infrared radiation emitted by said second zone;
the second scanner is configured to scan a third zone of the surface of the part with the first heat input element, and to perform the scanning along a plurality of lines substantially parallel to the second direction;
the second photosensitive surface element is configured to acquire images of the infrared radiation emitted by said third zone;
the first and second scanners being arranged to scan the second and third zones simultaneously.

20. The unit according to claim 19, wherein it comprises a computer programmed to perform:
a first processing step, in which first and/or second final images of the second zone are calculated respectively from images of the infrared radiation emitted by said second zone and respectively collected by the first and/or second photosensitive surface elements, respectively during the first and/or second sequences;
a second processing step, in which any structural defects in the second zone are detected by using the first and/or second final images obtained in the first processing step.

21. The unit according to claim 20, wherein
a) the first scanner is arranged so that the first heat input element scans the second zone while occupying, at a plurality of successive moments, a plurality of successive positions, and the acquirer is programmed so that the first photosensitive surface element acquires a plurality of images of the infrared radiation emitted by the second zone at said plurality of moments; and/or
b) the second scanner is arranged so that the second heat input element scans the second zone while occupying, at a plurality of successive moments, a plurality of successive positions, and the acquirer is programmed so that the second photosensitive surface element acquires a plurality of images of the infrared radiation emitted by the second zone at said plurality of moments;
the computer being programmed to carry out the following operations during the first processing step :
c) for each image acquired by the first photosensitive surface element, determining the given moment from the plurality of moments at which that image was acquired and extracting, from said image, a plurality of first points corresponding to the position of the first heat input element at a second given moment, the second given moment being equal to the given moment plus a predetermined time shift ; constituting the first final image by superimposing the first point extracted from all of the images acquired by the first photosensitive surface element ; and/or
d) for each image acquired by the second photosensitive surface element, determining the given moment from the plurality of moments at which said image was acquired and extracting, from said image, a plurality of second points corresponding to the position of the second heat input element at a second given moment, the second given moment being equal to the given moment plus a predetermined time shift ; constituting the second final image by superimposing the second points extracted from all of the images acquired by the second photosensitive surface element.

22. The unit according to claim 18, wherein the second direction is substantially parallel to the first direction, the first heat input element being a line forming, with the first direction, an angle comprised between 20° and 70°, the second heat input element being a line forming, with the second direction, an angle comprised between 110° and 160°.

23. The unit according to claim 22, further comprising a computer programmed to perform:
a first processing step, in which first and/or second final images of the second zone are calculated respectively from images of the infrared radiation emitted by said second zone and respectively collected by the first and/or second photosensitive surface elements, respectively during the first and/or second sequences;
a second processing step, in which any structural defects in the second zone are detected by using the first and/or second final images obtained in the first processing step ; and wherein
a) the first scanner is arranged so that the first heat input element scans the second zone while occupying, at a plurality of successive moments, a plurality of successive positions, and the acquirer is programmed so that the first photosensitive surface element acquires a plurality of first images of the infrared radiation emitted by the second zone at said plurality of moments;
wherein the computer is programmed to carry out the following operations during the first processing step:
c1) for each first image acquired by the first photosensitive surface element, determining the given moment from the plurality of moments at which said first image was acquired and extracting, from said first image, a line of first points corresponding to the position of the first heat input element at a second given moment, the line comprising a first upstream end point situated furthest along the first direction and a first downstream end point shifted relative to the first upstream end point opposite the first direction and along a first transverse direction perpendicular to the first direction, each first point having a measured intensity representative of the temperature of the surface of the part in a zone corresponding to said first point;
c2) establishing a first differential line by assigning each first point a differential intensity equal to the measured intensity minus the intensity of another point of the first image shifted along the first transverse direction relative to said first point and shifted along the first direction relative to the line;
c3) constituting the first final image by superimposing the first differential lines established for all of the first images acquired by the first photosensitive surface element.

24. The unit according to claim 23, wherein, in step c2), the other point is one of the first points of the line.

25. The unit according to claim 23, further comprising a computer programmed to perform:
a first processing step, in which first and/or second final images of the second zone are calculated respectively from images of the infrared radiation emitted by said second zone and respectively collected by the first and/or second photosensitive surface elements, respectively during the first and/or second sequences;

a second processing step, in which any structural defects in the second zone are detected by using the first and/or second final images obtained in the first processing step; and wherein b) the second scanner is arranged so that the second heat input element scans the second zone while occupying, at a plurality of successive moments, a plurality of successive positions, and the acquirer is programmed so that the second photosensitive surface element acquires a plurality of second images of the infrared radiation emitted by the second zone at said plurality of moments; and wherein the computer is programmed to carry out the following operations during the first processing step:

d1) for each second image acquired by the second photosensitive surface element, determining the given moment from the plurality of moments at which said second image was acquired and extracting, from said second image, a line of second points corresponding to the position of the second heat input element at a second given moment, the line comprising a second upstream end point situated furthest along the second direction and a second downstream end point shifted relative to the second upstream end point opposite the second direction and along a second transverse direction perpendicular to the second direction, each second point having a measured intensity representative of the temperature of the surface of the part in a zone corresponding to said second point;

d2) establishing a second differential line by assigning each second point a differential intensity equal to the measured intensity minus the value of another point of the second image shifted along the second transverse direction relative to said second point and shifted along the second direction relative to the line;

d3) constituting the second final image by superimposing the second differential lines established for all of the second images acquired during the second sequence, and wherein the second given moment is equal to the given moment plus a predetermined time shift, the second given moment being equal to the given moment plus a predetermined time shift.

26. The unit according to claim 22, further comprising a computer programmed to perform:

a first processing step, in which first and/or second final images of the second zone are calculated respectively from images of the infrared radiation emitted by said second zone and respectively collected by the first and/or second photosensitive surface elements, respectively during the first and/or second sequences;

a second processing step, in which any structural defects in the second zone are detected by using the first and/or second final images obtained in the first processing step; and wherein b) the second scanner is arranged so that the second heat input element scans the second zone while occupying, at a plurality of successive moments, a plurality of successive positions, and the acquirer is programmed so that the second photosensitive surface element acquires a plurality of second images of the infrared radiation emitted by the second zone at said plurality of moments;

and wherein the computer is programmed to carry out the following operations during the first processing step :

d1) for each second image acquired by the second photosensitive surface element, determining the given moment from the plurality of moments at which said second image was acquired and extracting, from said second image, a line of second points corresponding to the position of the second heat input element at a second given moment, the line comprising a second upstream end point situated furthest along the second direction and a second downstream end point shifted relative to the second upstream end point opposite the second direction and along a second transverse direction perpendicular to the second direction, each second point having a measured intensity representative of the temperature of the surface of the part in a zone corresponding to said second point;

d2) establishing a second differential line by assigning each second point a differential intensity equal to the measured intensity minus the value of another point of the second image shifted along the second transverse direction relative to said second point and shifted along the second direction relative to the line;

d3) constituting the second final image by superimposing the second differential lines established for all of the second images acquired during the second sequence.

27. The unit according to claim 26, wherein, in step d2), the other point is one of the first points of the line.

* * * * *